(12) United States Patent
Rack et al.

(10) Patent No.: US 11,897,895 B2
(45) Date of Patent: *Feb. 13, 2024

(54) PROCESS FOR PREPARING 2-EXO-(2-METHYLBENZYLOXY)-1-METHYL-4-ISOPROPYL-7-OXABICYCLO[2.2.1]HEPTANE

(71) Applicant: BASF AGRO B.V., Arnhem (NL)

(72) Inventors: Michael Rack, Ludwigshafen (DE); Stefan Benson, Ludwigshafen (DE); Bernd Wolf, Ludwigshafen (DE); Roland Goetz, Ludwigshafen (DE)

(73) Assignee: BASF AGRO B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/770,969

(22) PCT Filed: Dec. 6, 2018

(86) PCT No.: PCT/EP2018/083807
§ 371 (c)(1),
(2) Date: Jun. 9, 2020

(87) PCT Pub. No.: WO2019/115347
PCT Pub. Date: Jun. 20, 2019

(65) Prior Publication Data
US 2021/0163496 A1 Jun. 3, 2021

(30) Foreign Application Priority Data
Dec. 15, 2017 (EP) ..................................... 17207716

(51) Int. Cl.
*C07D 493/18* (2006.01)
(52) U.S. Cl.
CPC .................................. *C07D 493/18* (2013.01)
(58) Field of Classification Search
CPC ................................................... C07D 493/18
USPC ....................................................... 549/463
See application file for complete search history.

(56) References Cited

U.S. PATENT DOCUMENTS

| | | |
|---|---|---|
| 4,487,945 A | 12/1984 | Payne |
| 4,542,244 A | 9/1985 | Payne et al. |
| 4,670,041 A | 6/1987 | Payne et al. |

FOREIGN PATENT DOCUMENTS

| | | | |
|---|---|---|---|
| CN | 101602770 A | * | 12/2009 |
| EP | 0081893 A2 | | 6/1983 |
| WO | WO-2018/050518 A1 | | 3/2018 |
| WO | WO-2018/149676 A1 | | 8/2018 |
| WO | WO-2018/177907 A1 | | 10/2018 |
| WO | WO-2018/210662 A1 | | 11/2018 |
| WO | WO-2018/210663 A1 | | 11/2018 |

OTHER PUBLICATIONS

Lee et al. Metabolic Fate of Cnmethylin in Rats (Year: 1988).*
Tsukamoto, M., Kitamura, M., "Synthesis by Substitution" Science of Synthesis, (2008) 37, 47.*
Jursic "Synthetic Application of Micellar Catalysis. Williamson's Synthesis of Ethers" Tetrahedron, 1988 44(21), 6677-6680.*
Online: "https://www.thieme.de/en/thieme-chemistry/about-science-of-synthesis-54781.htm" Accessed Mar. 9, 2023.*
Paul et al. Indian Journal of Chemistry (1975), 13(12), 1338-40, (abstract only).*
Bredereck "Umsetzung N,N-disubstituierter Formamide mit Alkalimetallen" Angew. Chem. 1 77. Jahrg. 1965 1 Nr. 21 964-965.*
Online: "https://pr.vwr.com/store/product/28416702/toluene-acs" accessed Mar. 9, 2023.*
"The Pesticide Manual", 14th Edition, ed. Clive D. S. Tomlin, Nov. 1, 2006. pp. 195-196.

(Continued)

*Primary Examiner* — David K O'Dell
(74) *Attorney, Agent, or Firm* — MARSHALL, GERSTEIN & BORUN LLP

(57) ABSTRACT

This invention relates to a process for preparing (±)-2-exo-(2-Methylbenzyloxy)-1-methyl-4-isopropyl-7-oxabicyclo[2.2.1]heptane of the formula (I), any one of its individual enantiomers or any non-racemic mixture thereof any one of its individual enantiomers or any non-racemic mixture thereof, comprising the steps of (a) reacting (±)-2-exo-hydroxy-1-methyl-4-isopropyl-7-oxabicyclo[2.2.1]heptane of the formula (II), any one of its individual enantiomers or any non-racemic mixture thereof (as defined in the description) with elemental sodium to form a sodium salt of the formula (III), any one of its individual enantiomers or any non-racemic mixture thereof (as defined in the description), and (b) reacting said sodium salt (III) with a 2-Methylbenzyl compound of the formula (IV) wherein X is a leaving group, wherein the steps (a) and (b) are conducted in the presence of at least one substantially anhydrous inert organic solvent.

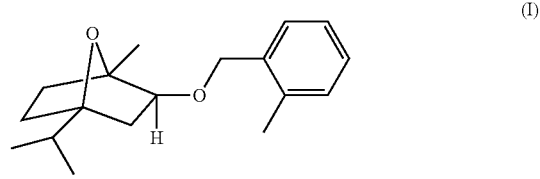

(I)

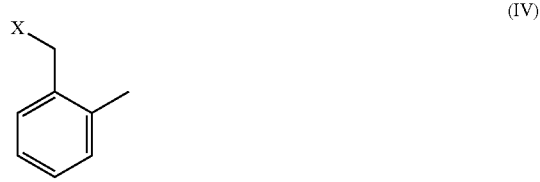

(IV)

18 Claims, No Drawings

(56) References Cited

OTHER PUBLICATIONS

Becker, et al., "Organikum, Organisch-chemisches Grundpraktikum", Wiley-VCH Verlag GmbH, 22 edition, 2004, pp. 237-241 & p. 589.
European Search Report for EP Patent Application No. 17207716.6, dated May 2, 2018, 3 pages.
International Patent Application No. PCT/EP2018/083807, International Search Report and Written Opinion, dated Jan. 30, 2019.
Lee, et al., "Metabolic fate of cinmethylin in rats", Journal of Agricultural and Food Chemistry, vol. 34, Issue 2, Mar. 1, 1986, pp. 162-170.
March, "Chapter 0-14: Alkylation with Alkyl Halides. The Williamson Reaction", Advanced Organic Chemistry, Second Edition, 1983, pp. 357-358.

* cited by examiner

PROCESS FOR PREPARING 2-EXO-(2-METHYLBENZYLOXY)-1-METHYL-4-ISOPROPYL-7-OXABICY-CLO[2.2.1]HEPTANE

This invention relates to a process for preparing (±)-2-exo-(2-Methylbenzyloxy)-1-methyl-4-isopropyl-7-oxabicyclo[2.2.1]heptane of the formula (I), any one of its individual enantiomers or any non-racemic mixture thereof by benzylating (±)-2-exo-hydroxy-1-methyl-4-isopropyl-7-oxabicyclo[2.2.1]heptane of the formula (II), any one of its individual enantiomers or any non-racemic mixture thereof with a 2-Methylbenzyl compound of the formula (V) in the presence of a substantially anhydrous inert organic solvent wherein the compound (II) is first reacted with elemental sodium to form the sodium salt of the compound (II) and said sodium salt is subsequently reacted with the compound (IV).

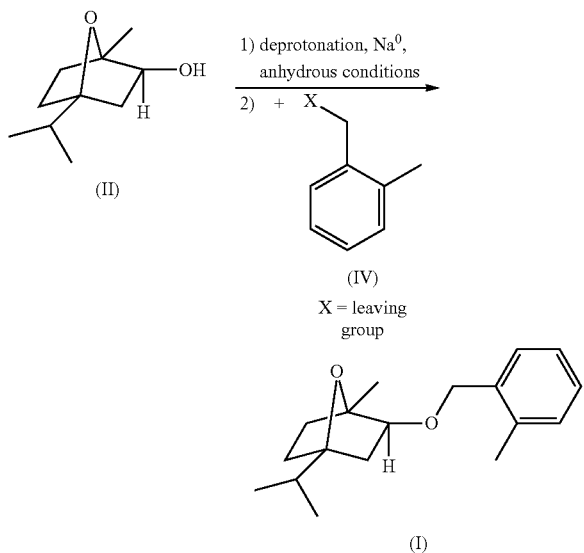

The racemic mixture (±)-2-exo-(2-Methylbenzyloxy)-1-methyl-4-isopropyl-7-oxabicyclo[2.2.1]heptane is a known herbicidal compound which has been developed for use in rice. It is described in the The Pesticide Manual, Fourteenth Edition, Editor: C. D. S. Tomlin, British Crop Production Council, 2006, entry 157, pages 195-196 with its common name Cinmethylin, its IUPAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methylphenyl)methoxy]-7-oxabicyclo[2.2.1]heptane.

The racemic mixture (±)-2-exo-(2-Methylbenzyloxy)-1-methyl-4-isopropyl-7-oxabicyclo[2.2.1]heptane (herein also referred to as the "exo-(±)-isomers", CAS RN 87818-31-3)

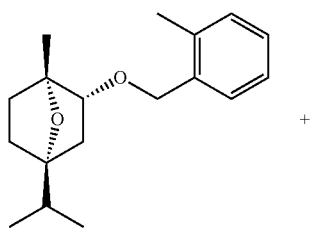

+

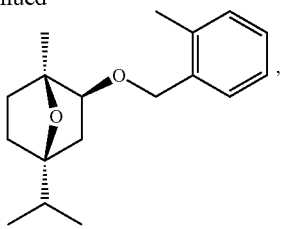

contains equal parts of the two enantiomers (+)-2-exo-(2-Methylbenzyloxy)-1-methyl-4-isopropyl-7-oxabicyclo[2.2.1]heptane (herein also referred to as the "exo-(+)-isomer", CAS RN 87818-61-9) and (−)-2-exo-(2-Methylbenzyloxy)-1-methyl-4-isopropyl-7-oxabicyclo[2.2.1]heptane (herein also referred to as the "exo-(−)-isomer", CAS RN 87819-60-1).

EP 0 081 893 A2 describes the preparation of (±)-2-exo-(2-Methylbenzyloxy)-1-methyl-4-isopropyl-7-oxabicyclo[2.2.1]heptane and its exo-(+)-isomer and exo-(−)-isomer by reacting (±)-2-exo-hydroxy-1-methyl-4-isopropyl-7-oxabicyclo[2.2.1]heptane with 2-methylbenzyl chloride in the presence of sodium hydride as a base and dimethylformamide as organic solvent (see Examples 29, 34, 35 and 62).

The use of sodium hydride as a base and dimethylformamide as organic solvent in the preparation of (±)-2-exo-(2-Methylbenzyloxy)-1-methyl-4-isopropyl-7-oxabicyclo[2.2.1]heptane by reacting (±)-2-exo-hydroxy-1-methyl-4-isopropyl-7-oxabicyclo[2.2.1]heptane with 2-methylbenzyl chloride is also described in U.S. Pat. No. 4,487,945 (see Embodiment 48), U.S. Pat. No. 4,542,244 (see Embodiment 219) and U.S. Pat. No. 4,670,041 (see Embodiment 219). Further, the preparation of the exo-(−)-isomer by reacting (−)-2-exo-hydroxy-1-methyl-4-isopropyl-7-oxabicyclo[2.2.1]heptane with 2-methylbenzyl chloride in any of the aforementioned references is conducted in the presence of sodium hydride as a base and N,N-dimethylacetamide as organic solvent (see U.S. Pat. No. 4,487,945, Embodiment 46; U.S. Pat. No. 4,542,244, Embodiment 218 and U.S. Pat. No. 4,670,041, Embodiment 218).

CN 101602770 A describes a three-step synthesis for the preparation of Cinmethylin. In steps 1 and 2, terpinen-4-ol is converted to the corresponding 1,2-epoxide which is then subjected to isomerization to give the 1,2-epoxide isomerization product. In final step 3, Cinmethylin is obtained by condensation of the 1,2-epoxide isomerization product in the presence of various combinations of bases and organic solvents (see Examples 1, 2, 3, 8 and 9: sodium hydroxide/ethyl acetate; Examples 4 and 5: sodium amide/dichloromethane; Example 6: sodium hydride/benzene and Example 7: sodium tert-butoxide/toluene).

Philip W. Lee et al., Journal of Agricultural and Food Chemistry, Vol. 34, No. 2, 1986, pages 162-170 discloses the preparation of a proposed cinmethylin metabolite, i.e. exo-2-[[2-(Chloromethyl) phenyl]methoxy]-1-methyl-4-(1-methylethyl)-7-oxabicyclo [2.2.1] heptane, by refluxing a solution of exo-1-methyl-4-(1-methylethyl)-7-oxabicyclo-[2.2.1]heptan-2-ol] in toluene and powdered sodium hydroxide under a Stark-Dean trap until no more water was removed. The resulting solution was subsequently reacted with α,α-dichloro-o-xylene to give a ca. 50:50 mixture of the mono- and disubstitution products along with the unreacted dichloroxylene. Purification of the reaction mixture gave exo-2-[[2-(Chloromethyl) phenyl]methoxy]-1-methyl-4-(1-methylethyl)-7-oxabicyclo [2.2.1] heptane in a low yield of 30%.

The above-mentioned prior art processes suffer from several drawbacks such as low selectivity due to the formation of relatively high amounts of undesired by-products such as e.g. di(2-methylbenzyl)ether, low yields and long reaction times leading to a low efficiency, high costs and high energy consumption. Further, in those processes that utilize alkali metal hydroxides as a base, water may be initially used as solvent but is also formed during the reaction which may lead to corrosion problems in the reactor. Further, agglomeration of salts and heavy deposit on the inner walls and other parts of the reactor such as e.g. baffles or agitator (herein also referred to as "fouling") can be observed during such reactions. This does not only decrease the rate of conversion but also leads to major difficulties on a large scale such as the prevention of proper heat transfer, heat removal and agitation in the reactor.

The aforementioned disadvantages make the prior art processes not very suitable for an industrial scale production and unattractive for economic and environmental reasons.

In view of the above drawbacks, there is still need for an improved process for the preparation of (±)-2-exo-(2-Methylbenzyloxy)-1-methyl-4-isopropyl-7-oxabicyclo[2.2.1] heptane of the formula (I), any of its individual enantiomers or any non-racemic mixture thereof, which would proceed in a more economical, eco-friendly and industrially viable manner.

It is therefore an object of the present invention to overcome or ameliorate at least one of the above disadvantages and thus to provide an improved and more economically and commercially feasible process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof.

Another object is to provide an industrially simple process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which gives the desired final product in good or even higher yields.

A further object is to provide an industrially simple process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which gives the desired final product in shorter reaction times with good or even higher yields.

Still another object is to provide a more environmentally friendly process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, by reducing unfavorable environmental effects such as e.g. high energy and material consumption.

Yet another object is to provide an industrially feasible process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which reduces or prevents the corrosion problems and the agglomeration of salts building up on the inner walls and other parts of the reactor during the reaction.

Still yet another object is to provide a process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which reduces the formation of undesirable by-products, such as, for example, di(2-methylbenzyl)ether.

It has now surprisingly been found that these and further objects are, in part or in whole, achieved by a process for preparing (±)-2-exo-(2-Methylbenzyloxy)-1-methyl-4-isopropyl-7-oxabicyclo[2.2.1]heptane of the formula (I)

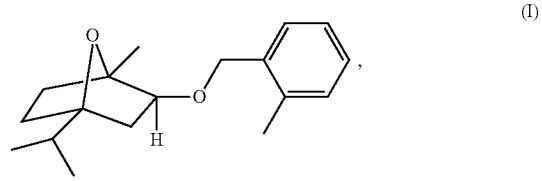 [SMILES: Cc1ccccc1COC1CC2(C(C)C)CCC1(C)O2]

any one of its individual enantiomers or any non-racemic mixture thereof comprising the steps of
(a) reacting (±)-2-exo-hydroxy-1-methyl-4-isopropyl-7-oxabicyclo[2.2.1]heptane of the formula (II)

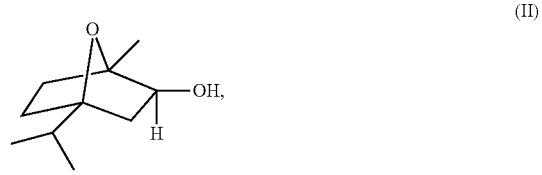

any one of its individual enantiomers or any non-racemic mixture thereof with elemental sodium to form a sodium salt of the formula (III)

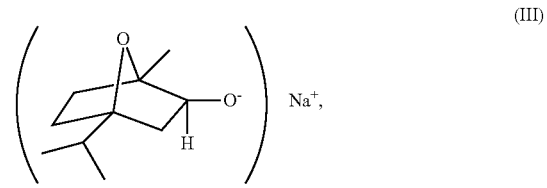

any one of its individual enantiomers or any non-racemic mixture thereof, and
(b) reacting the sodium salt of the formula (III), any of its individual enantiomers or any non-racemic mixture thereof with a 2-Methylbenzyl compound of the formula (IV)

wherein X is a leaving group,
wherein the steps (a) and (b) are conducted in the presence of at least one substantially anhydrous inert organic solvent.

Accordingly, the aforementioned process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof is a subject matter of the present invention.

The process according to the present invention entails a series of advantages and overcomes drawbacks of the prior art processes. One advantage is that the process of this invention provides high yields of the desired product, i.e. (±)-2-exo-(2-Methylbenzyloxy)-1-methyl-4-isopropyl-7-oxabicyclo[2.2.1]heptane of the formula (I), any of its individual enantiomers or any non-racemic mixture thereof, in a significantly shorter reaction time.

Another advantage is that the process of this invention leads to a higher selectivity to the final product (I) in that the formation of undesirable by-products such as e.g. di(2-methylbenzyl)ether can be reduced or prevented.

The process of this invention does not utilize alkali metal hydroxides as bases and is conducted under anhydrous conditions thus avoiding corrosion problems and the agglomeration of salts and heavy deposits on the inner walls and other parts of the reactor such as e.g. baffles or which would otherwise decrease the rate of conversion and lead to major difficulties on a large scale. Such reactor fouling virtually does not occur in the process of this invention because salts formed during the reaction are suspended in the reaction medium as finely divided particles.

Further, the unreacted starting material, in particular (±)-2-exo-hydroxy-1-methyl-4-isopropyl-7-oxabicyclo[2.2.1]heptane (II) which may also be used in excess amounts in the process of this invention, can be recovered and recycled more easily which leads to an economical and sustainable process.

Thus, the process of this invention reduces the energy consumption, costs and achieves high yields of the final product (I) by reducing or avoiding the formation of undesirable by-products.

In summary, the process of this invention allows the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof to proceed in an economical, eco-friendly and industrially viable manner.

Further embodiments of the invention are evident from the claims, the description and the examples. It is to be understood that the single features of the subject matter of the invention described herein can be applied not only in the combination given in each particular case but also in other combinations, without leaving the scope of the invention.

The materials used in the process of this invention are known compounds that are commercially available or can be prepared in a known manner.

For example, (±)-2-exo-hydroxy-1-methyl-4-isopropyl-7-oxabicyclo[2.2.1]heptane of the formula (II), any of its individual enantiomers or any non-racemic mixture thereof can be prepared by any of the methods described in EP 0 081 893 A2 (see Example 15), U.S. Pat. No. 4,487,945 (see Embodiments 1 and 45), U.S. Pat. No. 4,542,244 (see Embodiments 1 and 217) and U.S. Pat. No. 4,670,041 (see Embodiments 1 and 217) or in an analogous manner.

In the 2-Methylbenzyl compound of the formula (IV), the substituent X is a leaving group. The term "leaving group" as used herein refers to any group that departs the molecule with a pair of electrons in heterolytic bond cleavage such that the molecule is capable of participating in the nucleophilic substitution reaction of the process of this invention.

Preferred leaving groups X are selected from halogen, an oxygen linked leaving group, an ammonium group of the formula (V)

$$—N(R_1)(R_2)(R_3)^+Y^-  \quad (V)$$

wherein $R_1$, $R_2$ and $R_3$ are each independently selected from $C_1$-$C_6$-alkyl, $C_3$-$C_{10}$-cycloalkyl and $C_6$-$C_{20}$-aryl, and $Y^-$ is selected from halide, hydroxide, $C_1$-$C_4$-alkyl sulfonate and $C_6$-$C_{20}$-aryl sulfonate ions.

The organic moieties mentioned in the definition of certain variables (i.e. $R^1$, $R^2$, $R^3$, $R^4$, $R^5$, $R^6$, $R^7$, $R^8$, $R^9$, $R^{10}$, $R^{11}$, $X^-$, $Y^-$, $Z_1^-$ and $Z_2^-$), sulfonates (i.e. $C_1$-$C_4$-alkyl sulfonates, $C_1$-$C_4$-haloalkyl sulfonates, $C_6$-$C_{20}$-aryl sulfonates and $C_3$-$C_{10}$-cycloalkyl sulfonates) and specific groups of phase transfer catalysts (i.e. tetra-n-$C_1$-$C_4$-alkyl-ammonium chlorides, bromides, iodides, hydroxides, hydrogen sulfates or monomethyl sulfates, tetra-n-$C_1$-$C_8$-alkyl-ammonium chlorides, bromides, iodides, hydroxides, hydrogen sulfates or monomethyl sulfates and tetra-n-$C_1$-$C_{12}$-alkyl-ammonium chlorides, bromides, iodides, hydroxides, hydrogen sulfates or monomethyl sulfates) are—like the term halogen—collective terms for individual enumerations of the individual group members. The term "halogen" denotes in each case fluorine, chlorine, bromine or iodine. All hydrocarbon chains, e.g. alkyl chains, can be straight-chain or branched, the prefix $C_n$-$C_m$ denoting in each case the possible number of carbon atoms in the group. Examples of such meanings are:

$C_1$-$C_4$-alkyl: for example methyl, ethyl, n-propyl, isopropyl (—CH(CH$_3$)$_2$), n-butyl, sec-butyl (—CH(CH$_3$)—C$_2$H$_5$), isobutyl (—CH$_2$—CH(CH$_3$)$_2$) or tert-butyl (—C(CH$_3$)$_3$);

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$C_1$-$C_8$-alkyl: $C_1$-$C_6$-alkyl as mentioned above, and also, for example, n-heptyl, n-octyl or 2-ethylhexyl;

$C_1$-$C_{12}$-alkyl: $C_1$-$C_8$-alkyl as mentioned above, and also, for example, n-nonyl, iso-nonyl, n-decyl, n-undecyl or n-dodecyl;

$C_1$-$C_{20}$-alkyl: $C_1$-$C_{12}$-alkyl as mentioned above, and also, for example, n-tridecyl, n-tetradecyl, n-pentadecyl, n-hexadecyl, n-heptadecyl, n-octadecyl, n-nonadecyl or eicosyl;

$C_1$-$C_4$-haloalkyl: a $C_1$-$C_4$-alkyl as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl or 1-trifluoromethyl-1,2,2,2-tetrafluoroethyl; and $C_3$-$C_{10}$-cycloalkyl: for example cyclopropyl, cyclobutyl, cyclopentyl, cyclohexyl, cycloheptyl, cyclooctyl, cyclononyl or cyclodecyl.

The term "$C_6$-$C_{20}$-aryl" as used herein refers to an unsaturated aromatic carbocyclic group of from 6 to 20 carbon atoms having a single ring (e.g., phenyl) or multiple condensed (fused) rings, wherein at least one ring is aromatic (e.g. naphthalenyl or dihydrophenanthrenyl). Examples of $C_6$-$C_{20}$-aryls include phenyl, p-toluenyl, 1-naphthalenyl (1-naphthyl), 2-naphthalenyl (2-naphthyl), anthracenyl, indenyl or phenanthrenyl. A preferred $C_6$-$C_{20}$-aryl group is phenyl.

The term "$C_6$-$C_{20}$-aryl-$C_1$-$C_4$-alkyl-" as used herein includes but is not limited to benzyl, naphthylmethyl or xylyl. A preferred $C_6$-$C_{20}$-aryl-$C_1$-$C_4$-alkyl group is benzyl.

The term "a 5- or 6-membered heterocyclyl group containing 1, 2 or 3 heteroatoms selected from the group consisting of O, N and S" as used herein includes but is not limited to 1-piperidyl, 2-piperidyl, 3-piperidyl, 4-piperidyl, 4-morpholinyl and 4-methyl-1-piperidyl.

The term "halide ion" as used herein refers to e.g. a fluoride ion, a chloride ion, a bromide ion or an iodide ion.

Preferred oxygen linked leaving groups are selected from $C_1$-$C_4$-alkyl sulfonates, $C_1$-$C_4$-haloalkyl sulfonates, $C_6$-$C_{20}$-aryl sulfonates, $C_3$-$C_{10}$-cycloalkyl sulfonates and imidazolylsulfonate (imidazylate), more preferably from $C_1$-$C_4$-alkyl sulfonates, $C_1$-$C_4$-haloalkyl sulfonates and $C_6$-$C_{20}$-aryl sulfonates and even more preferably from $C_1$-$C_4$-alkyl sulfonates and $C_6$-$C_{20}$-aryl sulfonates.

Examples of $C_1$-$C_4$-alkyl sulfonates include but are not limited to mesylate (methanesulfonate), esylate (ethanesulfonate), n-propylsulfonate, iso-propylsulfonate, n-butylsulfonate, iso-butylsulfonate, sec-butylsulfonate and tert-butylsulfonate.

Examples of $C_1$-$C_4$-haloalkyl sulfonates include but are not limited to triflate (trifluoromethanesulfonate) and trichloromethanesulfonate.

Examples of $C_6$-$C_{20}$-aryl sulfonates include but are not limited to tosylate (p-toluenesulfonate), besylate (benzenesulfonate) and 2-naphtyl sulfonate.

Examples of $C_3$-$C_{10}$-cycloalkyl sulfonates include but are not limited to cyclohexylsulfonate.

Preferably, the oxygen linked leaving group is selected from mesylate (methanesulfonate), esylate (ethanesulfonate), n-propylsulfonate, iso-propylsulfonate, n-butylsulfonate, iso-butylsulfonate, sec-butylsulfonate, tert-butylsulfonate, triflate (trifluoromethanesulfonate), trichloromethanesulfonate, tosylate (p-toluenesulfonate), besylate (benzenesulfonate), 2-naphtyl sulfonate, cyclohexylsulfonate and imidazolylsulfonate (imidazylate), more preferably from mesylate, esylate, triflate, tosylate and besylate and even more preferably from mesylate and tosylate.

In another preferred embodiment, the leaving group X is selected from halogen, a $C_1$-$C_4$-alkyl sulfonate, a $C_6$-$C_{20}$-aryl sulfonate and an ammonium group of the formula (V)

—N($R_1$)($R_2$)($R_3$)$^+Y^-$     (V)

wherein $R_1$, $R_2$ and $R_3$ are each independently selected from $C_1$-$C_6$-alkyl and $Y^-$ is selected from halide, hydroxide, $C_1$-$C_4$-alkyl sulfonate and $C_6$-$C_{20}$-aryl sulfonate ions.

More preferably, the leaving group X is selected from halogen, a $C_1$-$C_4$-alkyl sulfonate, a $C_6$-$C_{20}$-aryl sulfonate and an ammonium group of the formula (V) wherein $R_1$, $R_2$ and $R_3$ are each independently selected from $C_1$-$C_6$-alkyl and $Y^-$ is selected from a halide, hydroxide, mesylate and tosylate ion.

Even more preferably, the leaving group X is selected from halogen, a $C_1$-$C_4$-alkyl sulfonate, a $C_6$-$C_{20}$-aryl sulfonate and an ammonium group of the formula (V) wherein $R_1$, $R_2$ and $R_3$ are each independently selected from $C_1$-$C_6$-alkyl and $Y^-$ is selected from a halide ion (preferably a chloride ion).

Still more preferably, the leaving group X is selected from chlorine, bromine, iodine, mesylate, tosylate, a trimethyl ammonium chloride group of the formula (Va)

—N(CH$_3$)$_3^+$Cl$^-$     (Va), and a triethyl ammonium chloride group of the formula (Vb)

—N(CH$_2$CH$_3$)$_3^+$Cl$^-$     (Vb).

Yet more preferably, the leaving group X is selected from chlorine, bromine, iodine, mesylate, tosylate and a trimethyl ammonium chloride group of the formula (Va).

Still even more preferably, the leaving group X is selected from chlorine, mesylate, tosylate and a trimethyl ammonium chloride group of the formula (Va).

In another preferred embodiment, the leaving group X is selected from halogen, in particular from chlorine, bromine and iodine. Most preferably, the leaving group X is chlorine.

In yet another embodiment, the 2-Methylbenzyl compound of the formula (IV) is selected from the group consisting of 2-Methylbenzyl chloride (1-(chloromethyl)-2-methylbenzene) of the formula (IVa)

(IVa)

2-Methylbenzyl bromide (1-(bromomethyl)-2-methylbenzene) of the formula (IVb)

(IVb)

2-Methylbenzyl iodide (1-(iodomethyl)-2-methyl-benzene) of the formula (IVc)

(IVc)

2-Methylbenzyl mesylate ((2-Methylphenyl)methyl methanesulfonate) of the formula (IVd)

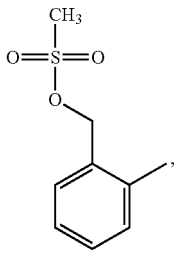
(IVd)

2-Methylbenzyl tosylate ((2-methylphenyl)methyl 4-methylbenzenesulfonate) of the formula (IVe)

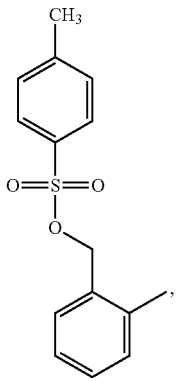
(IVe)

Trimethyl(o-tolylmethyl)ammonium chloride of the formula (IVf)

(IVf)

and
Triethyl(o-tolylmethyl)ammonium chloride of the formula (IVg)

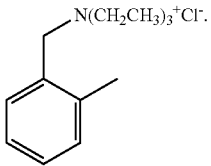
(IVg)

Most preferably, the 2-Methylbenzyl compound of the formula (IV) is 2-Methylbenzyl chloride (1-(chloromethyl)-2-methyl-benzene) of the formula (IVa).

The 2-Methylbenzyl compound of the formula (IV) used as a starting material in the process of this invention is either commercially available or can be prepared by methods known in the art or in an analogous manner.

For example, a 2-Methylbenzyl compound of the formula (IV) wherein X is halogen (such as e.g. 2-Methylbenzyl chloride of the formula (IVa)) may be prepared by the method described in Synthetic Communications, Volume 33, Issue 7, pages 1103-1107, 2003 or in an analogous manner.

For example, the 2-Methylbenzyl compound of the formula (IV) wherein X is a $C_1$-$C_4$-alkyl sulfonate or $C_6$-$C_{20}$-aryl sulfonate (such as e.g. 2-Methylbenzyl mesylate of the formula (IVd) or 2-Methylbenzyl tosylate of the formula (IVe)) may be prepared by methods described in Energy & Fuels, 21(3), pages 1695-1698, 2007 or Phosphorus, Sulfur and Silicon and the Related Elements, 184(5), pages 1161-1174, 2009.

The 2-Methylbenzyl compound of the formula (IV) wherein X is an ammonium group of the formula (V) (such as e.g. trimethyl(o-tolylmethyl)ammonium chloride of the formula (IVf) or triethyl(o-tolylmethyl)ammonium chloride of the formula (IVg)) may be prepared by methods analogous to those described in Organic Syntheses, Coll. Vol. 4, p.98 (1963); Vol. 38, p.5 (1958). For example, the 2-Methylbenzyl compound of the formula (IV) wherein X is selected from halogen (preferably chlorine, bromine or iodine and more preferably chlorine), a $C_1$-$C_4$-alkyl sulfonate (preferably mesylate) or a $C_6$-$C_{20}$-aryl sulfonate (preferably tosylate) is reacted with a tertiary amine of the formula $NR_1R_2R_3$ wherein $R_1$, $R_2$ and $R_3$ have the same meaning as in formula (V) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl) in a suitable solvent such as e.g. anhydrous ethanol.

The 2-Methylbenzyl compound of the formula (IV) wherein X is an ammonium group of the formula (V) (such as e.g. trimethyl(o-tolylmethyl)ammonium chloride of the formula (IVf) or triethyl(o-tolylmethyl)ammonium chloride of the formula (IVg)) can be added to the reaction mixture separately (i.e. as isolated substance or in solution of any suitable solvent), or formed in the reaction mixture in-situ.

When the in-situ formation of the 2-Methylbenzyl compound of the formula (IV) wherein X is an ammonium group of the formula (V) (such as e.g. trimethyl(o-tolylmethyl) ammonium chloride of the formula (IVf) or triethyl(o-tolylmethyl)ammonium chloride of the formula (IVg)) is desired, the step (b) or both steps (a) and (b) are conducted in the presence of at least one tertiary amine of the formula $NR_1R_2R_3$ wherein $R_1$, $R_2$ and $R_3$ have the same meaning as in formula (V) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl).

In particular, the 2-Methylbenzyl compound of the formula (IV) wherein X is an ammonium group of the formula (V) (such as e.g. trimethyl(o-tolylmethyl)ammonium chloride of the formula (Vf) or triethyl(o-tolylmethyl)ammonium chloride of the formula (IVg)) may be formed in-situ by reacting the 2-Methylbenzyl compound of the formula (IV) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) with a tertiary amine of the formula $NR_1R_2R_3$ wherein $R_1$, $R_2$ and $R_3$ have the same meaning as in formula (V) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl) in the process of this invention.

For this purpose, the tertiary amine of the formula $NR_1R_2R_3$ can be added to step (a), step (b) or both steps (a) and (b). When both steps (a) and (b) are conducted in the presence of at least one tertiary amine of the formula $NR_1R_2R_3$, said tertiary amine may only be added to step (a), i.e. without further addition to step (b), so that the unreacted tertiary amine can still be used in step (b). Alternatively, said tertiary amine may also be added to both steps (a) and (b). For example, one amount of said tertiary amine is added to step (a) and a second amount of said tertiary amine is added to step (b).

Examples of suitable tertiary amines of the formula $NR_1R_2R_3$ are tri-($C_1$-$C_6$)-alkylamines such as trimethylamine, triethylamine, tributylamine and N,N-diisopropylethylamine; di-($C_1$-$C_6$)-alkyl-phenylamines such as N,N-dimethylaniline and N,N-diethylaniline; and the like.

Preferably, a tertiary amine of the formula $NR_1R_2R_3$ is used wherein $R_1$, $R_2$ and $R_3$ are each $C_1$-$C_6$-alkyl, more preferably $C_1$-$C_4$-alkyl, in particular methyl or ethyl and most preferably methyl.

Thus, in an especially preferred embodiment, the tertiary amine of the formula $NR_1R_2R_3$ is selected from trimethylamine, triethylamine or a combination thereof. Most preferably, the tertiary amine of the formula $NR_1R_2R_3$ is trimethylamine.

It is envisioned that the tertiary amine $NR_1R_2R_3$ replaces the leaving group X in the 2-Methylbenzyl compound of the formula (IV) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) to form the respective ammonium-salt, i.e. the 2-Methylbenzyl compound of the formula (IV) wherein X is an ammonium group of the formula (V) (such as e.g. trimethyl(o-tolylmethyl)ammonium chloride of the formula (IVf) or triethyl(o-tolylmethyl)ammonium chloride of the formula (IVg)). The ammomium salt formed in-situ immediately reacts with the sodium salt of the formula (III), any of its individual enantiomers or any non-racemic mixture thereof being present in the reaction mixture. During this benzylation, the tertiary amine is released again and thus available for restarting the nucleophilic substitution of the 2-Methylbenzyl compound of the formula (IV) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine).

The aforementioned in-situ formation of the 2-Methylbenzyl compound of the formula (IV) wherein X is an ammomium group of the formula (V) is further illustrated in the following reaction scheme.

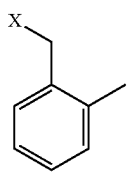

(IV)

X=halogen, $C_1$-$C_4$-alkyl sulfonate or $C_6$-$C_{20}$-aryl sulfonate

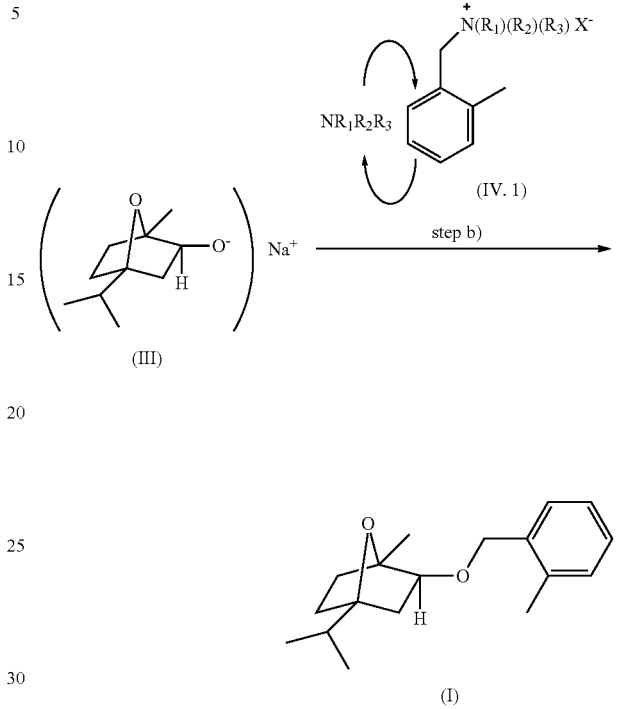

Hence, this variant of the process according to the invention is particularly advantageous because only substoichiometric or even catalytic amounts of the tertiary amine $NR_1R_2R_3$ relative to the 2-Methylbenzyl compound of the formula (IV) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) are required without discontinuing the benzylation reaction. Moreover, the higher electrophilicity due to the ionic nature of the 2-Methylbenzyl compound of the formula (IV) wherein X is an ammonium group of the formula (V) leads to an acceleration of the reaction as compared to directly using the 2-Methylbenzyl compound of the formula (IV) wherein X is selected from halogen, a $C_1$-$C_4$-alkyl sulfonate or a $C_6$-$C_{20}$-aryl sulfonate as the electrophilic reagent. Further, the amphiphilic character of the 2-Methylbenzyl compound of the formula (IV) wherein X is an ammonium group of the formula (V) is also beneficial given that the reaction medium forms a heterogeneous mixture comprising a liquid and solid phase.

The molar ratio of the 2-Methylbenzyl compound of the formula (IV) (in particular 2-Methylbenzyl chloride of the formula (IVa)) to ($\pm$)-2-exo-hydroxy-1-methyl-4-isopropyl-7-oxabicyclo[2.2.1]heptane of the formula (II), any one of its individual enantiomers or any non-racemic mixture thereof, in particular ($\pm$)-2-exo-hydroxy-1-methyl-4-isopropyl-7-oxabicyclo[2.2.1]heptane of the formula (II), can vary widely and depends on the nature of the 2-Methylbenzyl compound (IV) employed and the reaction conditions used, but is generally from 3:1 to 0.9:1, preferably from 2:1 to 0.9:1, more preferably from 1.5:1 to 0.9:1 and even more preferably from 1.1:1 to 0.9:1.

In step (a) of the process of this invention, (±)-2-exo-hydroxy-1-methyl-4-isopropyl-7-oxabicyclo[2.2.1]heptane of the formula (II), any one of its individual enantiomers or any non-racemic mixture thereof is reacted with elemental sodium to form a sodium salt of the formula (III)

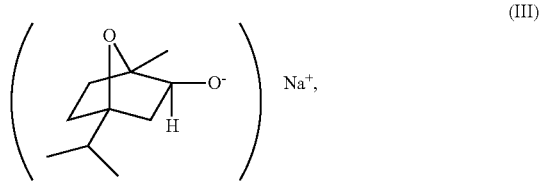

any one of its individual enantiomers or any non-racemic mixture thereof.

The chemical name of the sodium salt of formula (III) is sodium 4-isopropyl-1-methyl-7-oxabicyclo[2.2.1]heptan-2-olate.

The elemental sodium may be used in various forms, such as, for example, in any of the commercially available forms of sodium including but not limited to solid forms such as rods, cubes or pieces stored in a protective liquid such as, for example, mineral oil or paraffin oil, dispersions of sodium particles in an inert dispersing medium such as, for example, aliphatic and aromatic hydrocarbons (e.g. paraffin, toluene, xylenes or benzene), sodium metal powder or sodium sand. As another commercially available form of elemental sodium, liquid sodium may be mentioned which must be operated in a temperature range from the melting point of sodium (97.7° C.) to a temperature below the boiling point of sodium (873° C.).

The terms "elementary sodium", "metallic sodium", "sodium metal" and simply "sodium", "Na" or "Na⁰" may also be used herein and have the same meaning as defined herein for the term "elemental sodium".

Conventional processes for preparing alkali metal dispersions (e.g. a sodium dispersion) and alkali metal powders (e.g. a sodium powder) derived therefrom include the melting of the alkali metal (e.g. sodium) in a hydrocarbon oil and then agitating the molten metal in an inert hydrocarbon oil at dispersion speed in an inert atmosphere, usually nitrogen or argon. Dispersing aids, such as e.g. silicon oils, hydrocarbon polymers, ethers, alcohols, organic acids, carbon black and organic salts, can be used to facilitate rapid dispersion of the molten metal and development of uniform particle size. The finished dispersion is cooled, optionally separated from the hydrocarbon oil by washing the metal with an appropriate hydrocarbon solvent and stored under argon. An alternative process for preparing alkali metal dispersions forces molten alkali metal and argon through a high shear spray nozzle into hexane. Further details on conventional dispersion processes, dispersing aids and equipment can be found in "Alkali Metal Dispersions" by Irving Fatt and Marie Tashima, D. Van Nostrand Company (1961).

Elemental sodium may also be introduced into the reaction medium of step (a) in the form of a sodium alloy, preferably a liquid sodium alloy (e.g. a sodium-potassium alloy or a sodium-mercury alloy) which is either commercially available or can be prepared by methods known in the art, see e.g. Klemm, A., Hartmann, G. and Lange, L., Article "Sodium and Sodium Alloys" in Ullmann's Encyclopedia of Industrial Chemistry, Wiley-VCH (2000), pages 275 to 295.

In a preferred embodiment, the elemental sodium used in step (a) is present in the form of liquid sodium, dispersed sodium particles or a combination thereof, more preferably in the form of dispersed sodium particles.

In another preferred embodiment, the elemental sodium used in step (a) is present in the form of liquid sodium, a dispersion of sodium particles in an inert dispersing medium, or a combination thereof.

More preferably, the elemental sodium used in step (a) is present in the form of a dispersion of sodium particles in an inert dispersing medium.

Even more preferably, the elemental sodium used in step (a) is present in the form of a dispersion of sodium particles in an inert dispersing medium which is identical to the substantially anhydrous (preferably anhydrous) inert organic solvent used in steps (a) and (b).

Still more preferably, the elemental sodium used in step (a) is present in the form of a dispersion of sodium particles in the substantially anhydrous (preferably anhydrous) inert organic solvent used in steps (a) and (b).

Particularly preferably, the elemental sodium used in step (a) is present in the form of a dispersion of sodium particles in an inert organic solvent selected from hydrocarbons, preferably from aliphatic hydrocarbons, cycloaliphatic hydrocarbons, aromatic hydrocarbons and any combination thereof, more preferably from aliphatic hydrocarbons, aromatic hydrocarbons and any combination thereof and in particular from aromatic hydrocarbons.

Yet more preferably, the elemental sodium used in step (a) is present in the form of a dispersion of sodium particles in an inert organic solvent selected from n-heptane, toluene, o-xylene, m-xylene, p-xylene or any combination thereof (preferably in the form of a dispersion of sodium particles in toluene).

The concentration of the elemental sodium in the dispersion of sodium particles can vary and depends on the nature of the dispersing medium and the conditions used for its preparation, but is generally from 5 to 50% by weight, preferably 10 to 50% by weight and more preferably 30 to 50% by weight of elemental sodium, based on the weight of the dispersion.

In step (a), the molar ratio of the elemental sodium (calculated as 100% Na) to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), can vary widely and depends on the reaction conditions used, but is generally from 0.95:1 to 5:1, preferably from 0.95:1 to 3:1, more preferably from 0.95:1 to 2:1 and even more preferably from 0.95:1 to 1.1:1.

The steps (a) and (b) of the process of this invention are conducted in the presence of at least one substantially anhydrous (preferably anhydrous) inert organic solvent.

In a preferred embodiment, the steps (a) and (b) are conducted in the substantially anhydrous (preferably anhydrous) inert organic solvent. However, in another embodiment, the steps (a) and (b) may be conducted in different substantially anhydrous (preferably anhydrous) inert organic solvent as defined herein.

By the term "inert organic solvent" is meant an organic solvent which, under the reaction conditions of the process of this invention, does not enter into any appreciable reaction with either the reactants or the products.

The term "substantially anhydrous" as used herein generally means that, although anhydrous inert organic solvents are generally preferred in the reaction mixture, trace amounts of water, such as that often found in commercially available solvents, can be tolerated. Larger amounts of water should be avoided, since there would be an increased consumption of feedstocks and the danger of ignition of the metallic sodium. Further, the term "substantially anhydrous" as used herein means to have a water content lower than 5% by weight, preferably lower than 1% by weight, more preferably lower than 0.5% by weight, even more preferably lower than 0.1% by weight, still more preferably lower than 0.01% by weight, yet more preferably lower than 0.001% by weight and most preferably lower than 0.0001% by weight. Thus, the substantially anhydrous inert organic solvent has a water content lower than 5% by weight, preferably lower than 1% by weight, more preferably lower than 0.5% by weight, even more preferably lower than 0.1% by weight, still more preferably lower than 0.01% by weight, yet more preferably lower than 0.001% by weight and most preferably lower than 0.0001% by weight (in each case based on the total weight of the substantially anhydrous inert organic solvent).

The substantially anhydrous (preferably anhydrous) inert organic solvent used in the process of this invention can be selected from a variety of solvents depending upon the reaction conditions used.

Preferably, the substantially anhydrous (preferably anhydrous) inert organic solvent is selected from aprotic organic solvents. In particular, the aprotic organic solvent is selected from the group consisting of non-polar aprotic organic solvents, polar aprotic organic solvents, and any mixture thereof. Non-polar aprotic organic solvents are especially preferred. Especially preferable non-polar aprotic solvents include those which have a relative dielectric constant at 20° C. of less than 8, preferably of less than 6 and more preferably of less than 3.

Suitable substantially anhydrous (preferably anhydrous) inert organic solvents can be selected from hydrocarbons, amides, ethers, ketones, nitriles and any combination thereof, preferably from aliphatic hydrocarbons, cycloaliphatic hydrocarbons, aromatic hydrocarbons, amides, ethers, ketones, nitriles and any combination thereof.

In another preferred embodiment, the substantially anhydrous (preferably anhydrous) inert organic solvent is selected from hydrocarbons.

The hydrocarbon used as the substantially anhydrous (preferably anhydrous) inert organic solvent in this invention may be selected from aliphatic hydrocarbons, cycloaliphatic hydrocarbons, aromatic hydrocarbons and any combination thereof.

Preferably, the substantially anhydrous (preferably anhydrous) inert organic solvent can be selected from aliphatic hydrocarbons, cycloaliphatic hydrocarbons, aromatic hydrocarbons, amides, ethers, ketones, nitriles and any combination thereof.

The term "aliphatic hydrocarbons" includes straight and branched chain aliphatic hydrocarbons.

Straight chain aliphatic hydrocarbons that can be used in the present invention are those having from 7 to 15 carbon atoms, preferably 7 to 10 carbon atoms. Examples of straight chain aliphatic hydrocarbons include n-heptane, n-octane, n-nonane, n-decane or any combination thereof, preferably n-heptane.

The branched chain aliphatic hydrocarbons which are suitable for use in the present invention are those having from 8 to 15 carbon atoms, preferably 8 to 12 carbon atoms and more preferably 8 to 11 carbon atoms. Examples of suitable branched chain aliphatic hydrocarbons include 2,2,4-trimethylpentane, 2,4-dimethylhexane, 2,5-dimethylhexane, 2,2,4-trimethylhexane, 2,3,4-trimethylhexane, 3,3,4-trimethylhexane, 2-methylheptane, 3-methylheptane, 2,3-dimethylheptane, 3,4-dimethylpentane, 2-ethyloctane, 2,3-dimethyloctane, 2-methylnonane, 3,4-dimethylnonane, 3-methyldecane, 2-methylundecane, 2-methyldodecane, 2,2,4 trimethyldodecane and any combination thereof.

Especially suitable are mixtures of branched chain aliphatic hydrocarbons having from 7 to 12 carbon atoms and preferably 8 to 11 carbon atoms, such as the commercial mixtures of isoparaffinic hydrocarbons sold under the tradename Isopar® by ExxonMobil Chemical, such as for example Isopar® E. Isopar E is a mixture of isoparaffinic hydrocarbons with a distillation range of 113° C. to 139° C.

Examples of suitable cycloaliphatic hydrocarbons include saturated or unsaturated cycloaliphatic hydrocarbons, such as e.g. cycloheptane, cyclooctane, cyclooctene, 1,5-cyclooctadiene and the like. Preference is given to saturated cycloaliphatic hydrocarbons having from 7 to 10 carbon atoms. Cycloheptane is particularly preferred.

Examples of suitable aromatic hydrocarbons include toluene, o-xylene, m-xylene, p-xylene, ethylbenzene, 2-propylbenzene (cumene), 2-isopropyltoluene (o-cymol), 3-isopropyltoluene (m-cymol), 4-isopropyltoluene (p-cymol), 1,3,5-trimethylbenzene (mesitylene) and the like. Preference is given to toluene, o-xylene, m-xylene, p-xylene, ethylbenzene, 1,3,5-trimethylbenzene (mesitylene) and any combination thereof. Especially preferred among the aromatic hydrocarbons are toluene, o-xylene, m-xylene, p-xylene, 1,3,5-trimethylbenzene (mesitylene) and any combination thereof, with toluene being the most preferred.

Examples of suitable amides include N,N-dimethylformamide, dimethylacetamide, diethylacetamide and the like.

Examples of suitable ethers include acyclic, cyclic or aromatic ethers such as cyclopentyl methyl ether, 1,4-dioxane, anisole and the like.

Examples of suitable ketones include methyl isobutyl ketone, cyclopropyl methyl ketone and the like.

Examples of suitable nitriles include benzonitrile and the like.

In a preferred embodiment, the substantially anhydrous (preferably anhydrous) inert organic solvent is selected from aliphatic hydrocarbons, cycloaliphatic hydrocarbons, aromatic hydrocarbons, acyclic ethers, cyclic ethers, aromatic ethers and any combination thereof, more preferably from aliphatic hydrocarbons, aromatic hydrocarbons, and any combination thereof, and still more preferably from aromatic hydrocarbons.

In a more preferred embodiment, the substantially anhydrous (preferably anhydrous) inert organic solvent is selected from n-heptane, n-octane, n-nonane, n-decane, toluene, o-xylene, m-xylene, p-xylene, ethylbenzene, 1,3,5-trimethylbenzene (mesitylene) and any combination thereof.

In an even more preferred embodiment, the substantially anhydrous (preferably anhydrous) inert organic solvent is selected from n-heptane, n-octane, toluene, o-xylene, m-xylene, p-xylene, ethylbenzene, 1,3,5-trimethylbenzene (mesitylene) and any combination thereof.

Still more preferably, the substantially anhydrous (preferably anhydrous) inert organic solvent is selected from n-heptane, toluene, o-xylene, m-xylene, p-xylene and any combination thereof.

Particularly preferred substantially anhydrous (preferably anhydrous) inert organic solvents are alkylbenzenes which are mono-, di-, or trialkylsubstituted with each alkyl group containing 1 to 3 carbon atoms, in particular those selected from toluene, o-xylene, m-xylene, p-xylene, ethylbenzene, 1,3,5-trimethylbenzene (mesitylene) and any combination thereof and still more preferably selected from toluene, o-xylene, m-xylene, p-xylene and any combination thereof. Most preferably, the inert organic solvent is toluene.

In another embodiment, the substantially anhydrous (preferably anhydrous) inert organic solvent (or the inert dispersing medium, respectively) has a boiling point at atmospheric pressure (1 bar) of equal to or more than the melting point of sodium (97.7° C.), preferably more than the melting point of sodium (97.7° C.), more preferably more than 98° C., even more preferably more than 100° C., still more preferably more than 110° C. and yet more preferably more than 130° C.

In yet another embodiment, the substantially anhydrous (preferably anhydrous) inert organic solvent (or the inert dispersing medium, respectively) has a boiling point at atmospheric pressure (1 bar) of from the melting point of sodium (97.7° C.) to 200° C., preferably from the melting point of sodium (97.7° C.) to 150° C. and more preferably from the melting point of sodium (97.7° C.) to 130° C.

In yet another embodiment, the substantially anhydrous (preferably anhydrous) inert organic solvent (or the inert dispersing medium, respectively) has a boiling point at atmospheric pressure (1 bar) of from 98 to 200° C., preferably from 98 to 150° C. and more preferably from 98 to 130° C.

In yet another embodiment, the substantially anhydrous (preferably anhydrous) inert organic solvent (or the inert dispersing medium, respectively) has a boiling point at atmospheric pressure (1 bar) of from 100 to 200° C., preferably from 100 to 150° C. and more preferably from 100 to 130° C.

In yet another embodiment, the substantially anhydrous (preferably anhydrous) inert organic solvent (or the inert dispersing medium, respectively) has a boiling point at atmospheric pressure (1 bar) of from 110 to 200° C., preferably from 110 to 150° C. and more preferably from 110 to 130° C.

The molar ratio of the substantially anhydrous (preferably anhydrous) inert organic solvent to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), can vary widely and depends on the reaction conditions used, but is generally from 30:1 to 1:1, preferably 20:1 to 1:1, more preferably from 15:1 to 1:1, even more preferably from 10:1 to 1:1 and still more preferably from 5:1 to 1:1.

In another embodiment, the molar ratio of the substantially anhydrous (preferably anhydrous) inert organic solvent selected from aromatic hydrocarbons (in particular toluene) to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), is 20:1 to 1:1, preferably 16:1 to 1:1, more preferably 15:1 to 1:1, even more preferably 13:1 to 2:1, yet more preferably 11:1 to 2:1, still more preferably 9:1 to 2:1 and in particular 6:1 to 3:1.

In another embodiment, the molar ratio of the substantially anhydrous (preferably anhydrous) inert organic solvent (preferably selected from aromatic hydrocarbons, in particular toluene) to the elemental sodium (calculated as 100% Na) is 20:1 to 1:1, preferably 16:1 to 1:1, more preferably 13:1 to 1:1, even more preferably 10:1 to 1:1, yet more preferably 9:1 to 2:1 and in particular 6:1 to 2:1.

In a preferred embodiment, the step (a) and/or step (b) (preferably the step (b)) of the process of the present invention is conducted in the presence of at least one phase-transfer catalyst.

Phase transfer catalysts suitable for use in the process of this invention are those well known in the art. Preferred phase transfer catalysts are selected from quarternary ammonium salts, quarternary pyridinium salts, quarternary phosphonium salts and any combination thereof and more preferably selected from quarternary ammonium salts, quarternary phosphonium salts and any combination thereof.

More preferably, the phase transfer catalyst is selected from quaternary ammonium salts of the general formula (VI)

     (VI)

wherein $R^4$, $R^5$, $R^6$ and $R^7$ are the same or different and are each independently selected from the group consisting of $C_1$-$C_{20}$-alkyl, $C_3$-$C_{10}$-cycloalkyl, $C_6$-$C_{20}$-aryl and $C_6$-$C_{20}$-aryl-$C_1$-$C_4$-alkyl, and $Z_1^-$ is a monovalent anion, quarternary phosphonium salts of the general formula (VII)

     (VII)

wherein $R^8$, $R^9$, $R^{10}$, and $R^{11}$ are the same or different and are each independently selected from a 5- or 6-membered heterocyclyl group containing 1, 2 or 3 heteroatoms selected from the group consisting of O, N and S, and $Z_2^-$ is a monovalent anion, and any combination thereof.

In a preferred embodiment, the monovalent anion $Z_1^-$ is selected from a halide, hydroxide, hydrogen sulfate and monomethyl sulfate, more preferably from chloride, bromide, iodide and hydroxide, even more preferably from chloride or bromide and is most preferably chloride.

In another preferred embodiment, the monovalent anion $Z_1^-$ is selected from a halide, more preferably from chloride or bromide is most preferably chloride.

In yet another preferred embodiment, the monovalent anion $Z_2^-$ is selected from a halide, hydroxide, hydrogen sulfate and monomethyl sulfate, more preferably from chloride, bromide, iodide and hydroxide, even more preferably from chloride or bromide and is most preferably chloride.

In still another preferred embodiment, the monovalent anion $Z_2^-$ is selected from a halide, more preferably from chloride or bromide and is most preferably chloride.

In a preferred embodiment, the phase transfer catalyst is selected from quaternary ammonium salts of the general formula (V) wherein $R^4$, $R^5$, $R^6$ and $R^7$ are the same or different and are each independently selected from the group consisting of $C_1$-$C_{20}$-alkyl, $C_6$-$C_{20}$-aryl and $C_6$-$C_{20}$-aryl-$C_1$-$C_4$-alkyl-.

More preferably, the phase transfer catalyst is selected from quaternary ammonium salts of the general formula (V) wherein $R^4$, $R^5$, $R^6$ and $R^7$ are the same or different and are each independently selected from $C_1$-$C_{20}$-alkyl, even more preferably $C_1$-$C_{12}$-alkyl and still more preferably $C_1$-$C_6$-alkyl and yet more preferably $C_1$-$C_4$-alkyl.

Particularly preferred phase transfer catalysts useful for the process of this invention are tetra-n-$C_1$-$C_{12}$-alkyl-ammonium chlorides, bromides, iodides, hydroxides, hydrogen sulfates or monomethyl sulfates (in particular chlorides), preferably tetra-n-$C_1$-$C_8$-alkyl-ammonium chlorides, bromides, iodides, hydroxides, hydrogen sulfates or monomethyl sulfates (in particular chlorides), e.g. tetramethylammonium chloride, bromide, iodide, hydroxide, hydrogen sulfate or monomethyl sulfate (in particular chloride), tetraethylammonium chloride, bromide, iodide, hydroxide, hydrogen sulfate or monomethyl sulfate, tetra-n-propylammonium chloride, bromide, iodide, hydroxide, hydrogen sulfate or monomethyl sulfate, tetra-n-butylammonium chloride, bromide, iodide, hydroxide, hydrogen sulfate or monomethyl sulfate (in particular chloride), tetra-n-pentylammonium chloride, bromide, iodide, hydroxide, hydrogen sulfate or monomethyl sulfate (in particular chloride), tetra-n-hexylammonium chloride, bromide, iodide, hydroxide, hydrogen sulfate or monomethyl sulfate (in particular chloride), tetra-n-heptylammonium chloride, bromide, iodide, hydroxide, hydrogen sulfate or monomethyl sulfate (in particular chloride), tetra-n-octylammonium chloride, bromide, iodide, hydroxide, hydrogen sulfate or monomethyl sulfate (in particular chloride), methyl-tri-n-butylammonium chloride, bromide, iodide, hydroxide, hydrogen sulfate or monomethyl sulfate (in particular chloride), ethyl-trimethylammonium chloride, bromide, iodide, hydroxide, hydrogen sulfate or monomethyl sulfate (in particular chloride), n-propyl-trimethyl ammonium chloride, bromide, iodide, hydroxide, hydrogen sulfate or monomethyl sulfate (in particular chloride), methyl-triethyl ammonium chloride, bromide, iodide, hydroxide, hydrogen sulfate or monomethyl sulfate (in particular chloride), n-butyl-triethylammonium chloride, bromide, iodide, hydroxide, hydrogen sulfate or monomethyl sulfate (in particular chloride), tri-n-octylmethylammonium chloride, bromide, iodide, hydroxide, hydrogen sulfate or monomethyl sulfate (in particular chloride) and n-dodecyltrimethylammonium chloride, bromide, iodide, hydroxide, hydrogen sulfate or monomethyl sulfate (in particular chloride). Of these, the use of tetra-n-$C_1$-$C_4$-alkyl-ammonium chlorides, bromides, iodides, hydroxides, hydrogen sulfates or monomethyl sulfates (in particular chlorides) is preferred, in particular tetra-n-butylammonium chloride, bromide, iodide, hydroxide, hydrogen sulfate or monomethyl sulfate (more specifically chloride) and methyl-tri-n-butylammonium chloride, bromide, iodide, hydroxide, hydrogen sulfate or monomethyl sulfate (more specifically chloride).

Even more preferably, the phase transfer catalyst is selected from tetra-n-butylammonium chloride, tri-n-octylmethylammonium chloride, n-dodecyltrimethylammonium chloride, benzyl(tri-n-butyl)ammonium chloride, tetrakis(1-piperidyl)phosphonium chloride and any combination thereof.

The phase-transfer catalyst, which is usually solid in pure form, can be used as such or, preferably, in dissolved form. For example, a solution of the phase transfer catalyst in any of the aforementioned substantially anhydrous (preferably anhydrous) inert organic solvents such as e.g. aromatic or aliphatic hydrocarbons (e.g. toluene or n-heptane) may be used in step (b). In another embodiment, a solution of the phase transfer catalyst in the 2-Methylbenzyl compound of the formula (IV), in particular 2-Methylbenzyl chloride of the formula (IVa), is used in step (b). More specifically, the phase transfer catalyst is added to the reaction mixture obtained in step (a) as a solution in the 2-Methylbenzyl compound of the formula (IV), in particular 2-Methylbenzyl chloride of the formula (IVa).

The molar ratio of the phase transfer catalyst to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane (II), is generally from 0.25:1 to 0.005:1, preferably from 0.05:1 to 0.005:1.

The process of this invention can be carried out under atmospheric pressure or under slightly elevated or reduced pressure. Typically, the atmospheric pressure is employed. In another embodiment, the process of this invention is conducted under reduced pressure, preferably in a range of from 0.01 to 10 bar and more preferably 0.1 to 6 bar. It is preferred that steps (a) and (b) are conducted at the same pressure. However, in another embodiment, steps (a) and (b) may be conducted at different pressures selected from the ranges as defined hereinabove.

The temperature used in the process of this invention can vary widely and depends on a variety of factors such as, for example, the substantially anhydrous (preferably anhydrous) inert organic solvent and the pressure used. Under atmospheric pressure (1 bar), the temperature is generally from 0 to 200° C., preferably from 15 to 180° C., more preferably from 25 to 150° C. and even more preferably from 25 to 130° C.

In view of the use of elemental sodium, at least step (a) of the process of this invention (preferably only step (a) and from a practical standpoint both steps (a) and (b)) may be conducted in a protective environment, in particular in the presence of an inert gas. Suitable inert gases include but are not limited to helium, nitrogen, argon or any mixture thereof with preference being given to nitrogen.

It is preferred that steps (a) and (b) are conducted at different temperatures. In one embodiment, the temperatures used in steps (a) and (b) may be conducted at different temperatures selected from the ranges as defined hereinabove. More preferably, the step (a) is conducted at a temperature $T_1$ and the step (b) is conducted at a temperature $T_2$ wherein the temperature $T_1$ is higher than the temperature $T_2$. In particular, the temperature $T_1$ used in step (a) is from 98 to 200° C., preferably from 98 to 180° C., more preferably from 98 to 150° C. and even more preferably from 98 to 130° C., and the temperature $T_2$ used in step (b) is from 25 to 150° C., preferably from 25 to 120° C., more preferably from 25 to 100° C. and even more preferably from 25 to 90° C.

The reaction time can vary in a wide range and depends on a variety of factors such as, for example, temperature, pressure, or the reagents and auxiliary substances used. Typical reaction times are in the range of from 1 to 24 hours, preferably from 1 to 12 hours and more preferably from 1 to 5 hours.

In another embodiment, the step (a) comprises the steps of
(a1.1) providing a first mixture comprising (±)-2-exo-hydroxy-1-methyl-4-isopropyl-7-oxabicyclo[2.2.1]heptane of the formula (II), any of its individual enantiomers or any non-racemic mixture thereof (preferably (±)-2-exo-hydroxy-1-methyl-4-isopropyl-7-oxabicyclo[2.2.1]heptane of the formula (II)), elemental sodium and the substantially anhydrous (preferably anhydrous) inert organic solvent, and
(a1.2) heating the first mixture to reflux to give a second mixture comprising the sodium salt of the formula (III), any of its individual enantiomers or any non-racemic mixture thereof.

In case the 2-Methylbenzyl compound of the formula (IV) wherein X is an ammonium group of the formula (V) (such as e.g. trimethyl(o-tolylmethyl)ammonium chloride of the formula (IVf) or triethyl(o-tolylmethyl)ammonium chloride of the formula (IVg)) is formed in-situ as described herein, a preferred embodiment of the step (a) comprises the steps of
(a2.1) providing a first mixture comprising (±)-2-exo-hydroxy-1-methyl-4-isopropyl-7-oxabicyclo[2.2.1]heptane of the formula (II), any of its individual enantiomers or any non-racemic mixture thereof (preferably (±)-2-exohydroxy-1-methyl-4-isopropyl-7-oxabicyclo[2.2.1]heptane of the formula (II)), elemental sodium, the substantially anhydrous (preferably anhydrous) inert organic solvent and the tertiary amine of the formula $NR_1R_2R_3$ wherein $R_1$, $R_2$ and $R_3$ have the same meaning as in formula (V) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl), and (a2.2) heating the first mixture to reflux to give a second mixture comprising the sodium salt of the formula (III), any of its individual enantiomers or any non-racemic mixture thereof.

In a preferred embodiment, the step (a) comprises the steps of (a3.1) providing a dispersion of sodium particles in an inert dispersing medium, preferably in the substantially anhydrous (preferably anhydrous) inert organic solvent as defined herein, (a3.2) heating said dispersion to reflux, and (a3.3) adding a solution of (±)-2-exo-hydroxy-1-methyl-4-isopropyl-7-oxabicyclo[2.2.1]heptane of the formula (II), any of its individual enantiomers or any non-racemic mixture thereof (preferably (±)-2-exo-hydroxy-1-methyl-4-isopropyl-7-oxabicyclo[2.2.1]heptane of the formula (II)) in the substantially anhydrous (preferably anhydrous) inert organic solvent to give a mixture comprising the sodium salt of the formula (III), any of its individual enantiomers or any non-racemic mixture thereof.

In a more preferred embodiment, the step (a) comprises the steps of (a4.1) melting of sodium in an inert dispersing medium, preferably in the substantially anhydrous (preferably anhydrous) inert organic solvent as defined herein, and then agitating the molten sodium in the inert dispersing medium to provide a dispersion of sodium particles in the inert dispersing medium, (a4.2) heating said dispersion to reflux, and (a4.3) adding a solution of (±)-2-exo-hydroxy-1-methyl-4-isopropyl-7-oxabicyclo[2.2.1]heptane of the formula (II), any of its individual enantiomers or any non-racemic mixture thereof (preferably (±)-2-exo-hydroxy-1-methyl-4-isopropyl-7-oxabicyclo[2.2.1]heptane of the formula (II)) in the substantially anhydrous (preferably anhydrous) inert organic solvent to give a mixture comprising the sodium salt of the formula (III), any of its individual enantiomers or any non-racemic mixture thereof.

In still another embodiment, the step (b) comprises the step of (b1) adding the 2-Methylbenzyl compound of the formula (IV) to the second mixture obtained in step (a1.2) or (a2.2) or the mixture obtained in step (a3.3) or (a4.3) under agitation to form the reaction mixture.

In yet another embodiment, the step (b) comprises the step of (b2) adding a mixture comprising the 2-Methylbenzyl compound of the formula (IV) (in particular 2-Methylbenzyl chloride of the formula (IVa)) and the phase transfer catalyst as defined herein (preferably a solution of the phase transfer catalyst as defined herein in the 2-Methylbenzyl compound of the formula (IV), in particular 2-Methylbenzyl chloride of the formula (IVa)) to the second mixture obtained in step (a1.2) or (a2.2) or the mixture obtained in step (a3.3) or (a4.3) under agitation to form the reaction mixture.

In case the 2-Methylbenzyl compound of the formula (IV) wherein X is an ammonium group of the formula (V) (such as e.g. trimethyl(o-tolylmethyl)ammonium chloride of the formula (IVf) or triethyl(o-tolylmethyl)ammonium chloride of the formula (IVg)) is formed in-situ as described herein, a preferred embodiment of the step (b) comprises the step of (b3) adding the 2-Methylbenzyl compound of the formula (IV) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) and the tertiary amine of the formula $NR_1R_2R_3$ wherein $R_1$, $R_2$ and $R_3$ have the same meaning as in formula (V) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl) to the second mixture obtained in step (a1.2) or (a2.2) or the mixture obtained in step (a3.3) or (a4.3) under agitation to form the reaction mixture.

The molar ratio of the tertiary amine of the formula $NR_1R_2R_3$ (in particular trimethylamine, triethylamine or a combination thereof, more preferably trimethylamine) to the 2-Methylbenzyl compound of the formula (IV) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) may be from 1:1 to 0.1:1, preferably from 0.5:1 to 0.1:1, more preferably from 0.25:1 to 0.1:1, even more preferably from 0.15:1 to 0.1:1 and yet more preferably 0.1:1 to 0.01:1.

In step (b) and more specifically in steps (b1), (b2) or (b3) as defined hereinabove, the 2-Methylbenzyl compound of the formula (IV) and/or the phase transfer catalyst as defined herein can be added batch-wise (in one or more individual portions) or continuously metered in, with preference being given to the continuous metered addition.

In another preferred embodiment, a mixture comprising the 2-Methylbenzyl compound of the formula (IV) (in particular 2-Methylbenzyl chloride of the formula (IVa)) and the phase transfer catalyst as defined herein (more preferably a solution of the phase transfer catalyst as defined herein in the 2-Methylbenzyl compound of the formula (IV), in particular 2-Methylbenzyl chloride of the formula (IVa)) is added in step (b) and more specifically in any one of steps (b1), (b2) and (b3) as defined hereinabove. Likewise, the mixture comprising the 2-Methylbenzyl compound of the formula (IV) (in particular 2-Methylbenzyl chloride of the formula (IVa)) and the phase transfer catalyst as defined herein (more preferably a solution of the phase transfer catalyst as defined herein in the 2-Methylbenzyl compound of the formula (IV), in particular 2-Methylbenzyl chloride of the formula (IVa)) can be added batch-wise (in one or more individual portions) or continuously metered in, with preference being given to the continuous metered addition.

(±)-2-exo-(2-Methylbenzyloxy)-1-methyl-4-isopropyl-7-oxabicyclo[2.2.1]heptane of the formula (I), any of its individual enantiomers or any non-racemic mixture thereof (preferably (±)-2-exo-(2-Methylbenzyloxy)-1-methyl-4-isopropyl-7-oxabicyclo[2.2.1]heptane of the formula (I)) is preferably isolated from the final reaction mixture obtained from step (b) by employing conventional methods, for example by extraction, in particular extraction with a basic or neutral aqueous medium, distillation, and the like.

The invention is illustrated by the following examples without being limited thereto or thereby.

EXAMPLE 1

Preparation of (±)-2-exo-(2-Methylbenzyloxy)-1-methyl-4-isopropyl-7-oxabicyclo[2.2.1]heptane by Using a Sodium Dispersion in Toluene, 0.95 Molar Equivalents of 1-(chloromethyl)-2-methyl-benzene, 0.025 Molar Equivalents of tetrakis(1-piperidyl) phosphonium chloride as Phase Transfer Catalyst Solid sodium (7.8 g, 0.34 mol) was dispersed in toluene (59.8 g, 0.65 mol). The reaction mixture was heated to reflux. Thereafter, a solution of (±)-2-exo-hydroxy-1-methyl-4-isopropyl-7-oxabicyclo[2.2.1]heptane (60.0 g, 0.35 mol) in toluene (89.8 g, 0.97 mol) was added to the sodium slurry over 40 minutes. The reaction mixture was cooled to 35° C. At this temperature tetrakis(1-piperidyl) phosphonium chloride (3.53 g, 0.01 mol) dissolved in 1-(chloromethyl)-2-methyl-benzene (46.8 g, 0.33 mol) was dosed to the reaction mixture within 2 hours. The reaction mixture was kept at 35° C. and 60 g water was added. After phase separation the organic phase was washed once with 1N HCl (60 mL), twice with 2N NaOH (60 mL) and once with water (60 mL). The product solution was azeotropically dried using Dean-Stark conditions. The product solution (259 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 33.9%. This corresponds to a yield of 95.6% of (±)-2-exo-(2-Methylbenzyloxy)-1-methyl-4-isopropyl-7-oxabicyclo[2.2.1]heptane.

COMPARATIVE EXAMPLE 1

Preparation of (±)-2-exo-(2-Methylbenzyloxy)-1-methyl-4-isopropyl-7-oxabicyclo[2.2.1]heptane by Using Solid Sodium Hydride in Toluene, 0.95 Molar Equivalents of 1-(chloromethyl)-2-methyl-benzene, 0.025 Molar Equivalents of tetrakis(1-piperidyl)phosphonium chloride as Phase Transfer Catalyst Solid sodium hydride (8.16 g, 0.34 mol) was dispersed in toluene (59.8 g, 0.65 mol). The reaction mixture was heated to reflux. Thereafter, a solution of (±)-2-exo-hydroxy-1-methyl-4-isopropyl-7-oxabicyclo[2.2.1]heptane (60.0 g, 0.35 mol) in toluene (89.8 g, 0.97 mol) was added to the sodium hydride slurry over 40 minutes. The reaction mixture was cooled to 35° C. At this temperature tetrakis(1-piperidyl)phosphonium chloride (3.53 g, 0.01 mol) dissolved in 1-(chloromethyl)-2-methyl-benzene (46.8 g, 0.33 mol) was dosed to the reaction mixture within 2 hours. The reaction mixture was kept at 35° C. and 60 g water was added. After phase separation the organic phase was washed once with 1N HCl (60 mL), twice with 2N NaOH (60 mL) and once with water (60 mL). The product solution was azeotropically dried using Dean-Stark conditions. The product solution (292 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 26.2%. This corresponds to a yield of 89.2% of (±)-2-exo-(2-Methylbenzyloxy)-1-methyl-4-isopropyl-7-oxabicyclo[2.2.1]heptane.

COMPARATIVE EXAMPLE 2

Preparation of (±)-2-exo-(2-Methylbenzyloxy)-1-methyl-4-isopropyl-7-oxabicyclo[2.2.1]heptane by Using Solid Sodium Hydride Suspension in Mineral Oil (60%) in Toluene, 0.95 Molar Equivalents of 1-(chloromethyl)-2-methyl-benzene, 0.025 Molar Equivalents of tetrakis(1-piperidyl)phosphonium chloride as Phase Transfer Catalyst Solid sodium hydride suspension in mineral oil (60%) (13.7 g, 0.34 mol) was dispersed in toluene (59.8 g, 0.65 mol). The suspension was decanted three times with 50 mL toluene to remove the mineral oil. The reaction mixture was heated to reflux. Thereafter, a solution of (±)-2-exo-hydroxy-1-methyl-4-isopropyl-7-oxabicyclo[2.2.1]heptane (60.0 g, 0.35 mol) in toluene (89.8 g, 0.97 mol) was added to the sodium hydride slurry over 40 minutes. The reaction mixture was cooled to 35° C. At this temperature tetrakis (1-piperidyl)phosphonium chloride (3.53 g, 0.01 mol) dissolved in 1-(chloromethyl)-2-methyl-benzene (46.8 g, 0.33 mol) was dosed to the reaction mixture within 2 hours. The reaction mixture was kept at 35° C. and 60 g water was added. After phase separation the organic phase was washed once with 1N HCl (60 mL), twice with 2N NaOH (60 mL) and once with water (60 mL). The product solution was azeotropically dried using Dean-Stark conditions. The product solution (258 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 29.6%. This corresponds to a yield of 88.9% of (±)-2-exo-(2-Methylbenzyloxy)-1-methyl-4-isopropyl-7-oxabicyclo[2.2.1]heptane.

EXAMPLE 2

Preparation of (±)-2-exo-(2-Methylbenzyloxy)-1-methyl-4-isopropyl-7-oxabicyclo[2.2.1]heptane by Using a Sodium Dispersion in Toluene, 0.95 Molar Equivalents of 1-(chloromethyl)-2-methyl-benzene, without Phase Transfer Catalyst Solid sodium (7.29 g, 0.32 mol) was dispersed in toluene (600 g, 6.5 mol). The reaction mixture was heated to reflux. Thereafter, a solution of (±)-2-exo-hydroxy-1-methyl-4-isopropyl-7-oxabicyclo[2.2.1]heptane (60.0 g, 0.35 mol) in toluene (89.8 g, 0.97 mol) was added to the sodium slurry over 40 minutes. At this temperature 1-(chloromethyl)-2-methyl-benzene (42.0 g, 0.3 mol) was dosed within 2 hours to the reaction mixture. The reaction mixture was cooled to 35° C. and 60 g water was added. After phase separation the organic phase was washed once with 1N HCl (60 mL), twice with 2N NaOH (60 mL) and once with water (60 mL). The toluene from the product solution was distilled off under reduced pressure. The product (87.9 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 72.9%. This corresponds to a yield of 77.8% of (±)-2-exo-(2-Methylbenzyloxy)-1-methyl-4-isopropyl-7-oxabicyclo[2.2.1]heptane.

EXAMPLE 3

Preparation of (±)-2-exo-(2-Methylbenzyloxy)-1-methyl-4-isopropyl-7-oxabicyclo[2.2.1]heptane by Using a Sodium Dispersion in Toluene, 0.95 Molar Equivalents of 1-(chloromethyl)-2-methyl-benzene, 0.025 Molar Equivalents of tetra-n-butylammonium chloride as Phase Transfer Catalyst Solid sodium (7.8 g, 0.34 mol) was dispersed in toluene (59.8 g, 0.65 mol). The reaction mixture was heated to reflux. Thereafter, a solution of (±)-2-exo-hydroxy-1-methyl-4-isopropyl-7-oxabicyclo[2.2.1]heptane (60.0 g, 0.35 mol) in toluene (89.8 g, 0.97 mol) was added to the sodium slurry over 40 minutes. The reaction mixture was cooled to 35° C. At this temperature tetra-n-butylammonium chloride (2.4 g, 0.01 mol) dissolved in 1-(chloromethyl)-2-methyl-benzene (46.8 g, 0.33 mol) was dosed within 2 hours to the reaction mixture. The reaction mixture was kept at 35° C. and 60 g water was added. After phase separation the organic phase was washed once with 1N HCl (60 mL), twice with 2N NaOH (60 mL) and once with water (60 mL). The product solution was azeotropically dried using Dean-Stark conditions. The product solution (266.8 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 31.5%. This corresponds to a yield of 91.4% of (±)-2-exo-(2-Methylbenzyloxy)-1-methyl-4-isopropyl-7-oxabicyclo[2.2.1]heptane.

EXAMPLE 4

Preparation of (±)-2-exo-(2-Methylbenzyloxy)-1-methyl-4-isopropyl-7-oxabicyclo[2.2.1]heptane by Using a Sodium Dispersion in Toluene, 0.95 Molar Equivalents of 1-(chloromethyl)-2-methyl-benzene, 0.025 Molar Equivalents of tri-n-octylmethylammonium chloride as Phase Transfer Catalyst Solid sodium (7.8 g, 0.34 mol) was dispersed in toluene (30.9 g, 0.33 mol). The reaction mixture was heated to reflux. Thereafter, a solution of (±)-2-exo-hydroxy-1-methyl-4-isopropyl-7-oxabicyclo[2.2.1]heptane (60.0 g, 0.35 mol) in toluene (89.8 g, 0.97 mol) was added to the sodium slurry over 40 minutes. The reaction mixture was cooled to 35° C. At this temperature tri-n-octylmethylammonium chloride (3.5 g, 0.01 mol) dissolved in 1-(chloromethyl)-2-methyl-benzene (46.8 g, 0.33 mol) was dosed within 2 hours to the reaction mixture. The reaction mixture was kept at 35° C. and 60 g water was added. After phase separation the organic phase was washed once with 1N HCl (60 mL), twice with 2N NaOH (60 mL) and once with water (60 mL). The product solution was azeotropically dried using Dean-Stark conditions. The product solution (262.9 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 30.7%. This corresponds to a yield of 87.9% of (±)-2-exo-(2-Methylbenzyloxy)-1-methyl-4-isopropyl-7-oxabicyclo[2.2.1]heptane.

EXAMPLE 5

Preparation of (±)-2-exo-(2-Methylbenzyloxy)-1-methyl-4-isopropyl-7-oxabicyclo[2.2.1]heptane by Using a Sodium Dispersion in n-heptane, 0.95 Molar Equivalents of 1-(chloromethyl)-2-methyl-benzene, 0.025 Molar Equivalents of tetra-n-butylammonium chloride as Phase Transfer Catalyst Solid sodium (8.06 g, 0.35 mol) was dispersed in n-heptane (47.4 g, 0.47 mol). The reaction mixture was heated to reflux. Thereafter, a solution of (±)-2-exo-hydroxy-1-methyl-4-isopropyl-7-oxabicyclo[2.2.1]heptane (60.0 g, 0.35 mol) in n-heptane (68.5 g, 0.68 mol) was added to the sodium slurry over 40 minutes. The reaction mixture was cooled to 35° C. At this temperature tetra-n-butylammonium chloride (2.4 g, 0.01 mol) dissolved in 1-(chloromethyl)-2-methyl-benzene (46.8 g, 0.33 mol) was dosed within 2 hours to the reaction mixture. The reaction mixture was kept at 35° C. and 60 g water was added. After phase separation the organic phase was washed once with 1N HCl (60 mL), twice with 2N NaOH (60 mL) and once with water (60 mL). The product solution was azeotropically dried using Dean-Stark conditions. The product solution (206.2 g) was analyzed via quantitative gas chromatography (GC) (GC with internal standard) and showed a (±)-2-exo-(2-Methylbenzyloxy)-1-methyl-4-isopropyl-7-oxabicyclo[2.2.1]heptane concentration of 38.2%. This corresponds to a yield of 85.7% of (±)-2-exo-(2-Methylbenzyloxy)-1-methyl-4-isopropyl-7-oxabicyclo[2.2.1]heptane.

The reactions as described in Examples 1 to 5 and Comparative Examples 1 and 2 hereinabove were conducted under a nitrogen gas atmosphere.

The invention claimed is:

1. A process for preparing (±)-2-exo-(2-Methylbenzyloxy)-1-methyl-4-isopropyl-7-oxabicyclo[2.2.1]heptane of the formula (I)

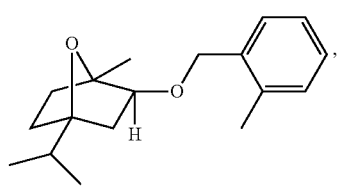

(I)

any one of its individual enantiomers or any non-racemic mixture thereof comprising the steps of (a) reacting (±)-2-exo-hydroxy-1-methyl-4-isopropyl-7-oxabicyclo[2.2.1]heptane of the formula (II)

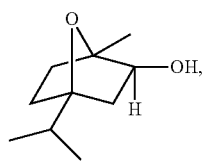

(II)

any one of its individual enantiomers or any non-racemic mixture thereof with elemental sodium to form a sodium salt of the formula (III)

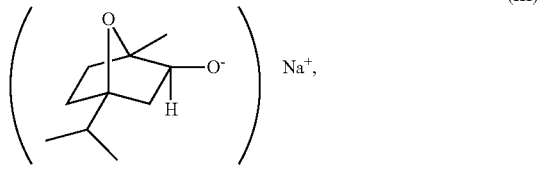

any one of its individual enantiomers or any non-racemic mixture thereof, and (b) reacting the sodium salt of the formula (III), any of its individual enantiomers or any non-racemic mixture thereof with a 2-Methylbenzyl compound of the formula (IV)

wherein X is a leaving group,
wherein the steps (a) and (b) are conducted in the presence of at least one substantially anhydrous inert organic solvent selected from hydrocarbons,
wherein the substantially anhydrous inert organic solvent has a water content lower than 0.1% by weight (Based on a total weight of the substantially anhydrous inert organic solvent, and
wherein the elemental sodium used in step (a) is present in the form of dispersed sodium particles and step (b) is conducted in the presence of at least one phase transfer catalyst selected from quaternary phosphonium salts.

2. The process according to claim 1, wherein the substantially anhydrous inert organic solvent is selected from aliphatic hydrocarbons, cycloaliphatic hydrocarbons, aromatic hydrocarbons and any combination thereof.

3. The process according to claim 1, wherein the substantially anhydrous inert organic solvent is selected from n-heptane, n-octane, cycloheptane, cyclooctane, toluene, o-xylene, m-xylene, p-xylene, ethylbenzene, 2-propylbenzene (cumene), 2-isopropyltoluene (o-cymol), 3-isopropyltoluene (m-cymol), 4-isopropyltoluene (p-cymol), 1,3,5-trimethylbenzene (mesitylene) and any combination thereof.

4. The process according to claim 1, wherein the elemental sodium used in step (a) is present in the form of a dispersion of sodium particles in an inert dispersing medium.

5. The process according to claim 4, wherein the inert dispersing medium of the dispersion of sodium particles is identical to the substantially anhydrous inert organic solvent used in steps (a) and (b).

6. The process according to claim 1, wherein the substantially anhydrous inert organic solvent and/or the inert dispersing medium has a boiling point of equal to or more than the melting point of sodium (97.7° C.).

7. The process according to claim 1, wherein the substantially anhydrous inert organic solvent has a water content lower than 0.01% by weight (based on the total weight of the substantially anhydrous inert organic solvent).

8. The process according to claim 1, wherein the molar ratio of the elemental sodium (calculated as 100% Na) to (±)-2-exo-hydroxy-1-methyl-4-isopropyl-7-oxabicyclo[2.2.1]heptane of the formula (II), any one of its individual enantiomers or any non-racemic mixture thereof is from 0.95:1 to 5:1.

9. The process according to claim 1, wherein the phase transfer catalyst is selected from
quaternary phosphonium salts of general formula (VII)

$$(R^8R^9R^{10}R^{11}P)^+Z_2^-  \quad (VII)$$

wherein $R^8$, $R^9$, $R^{10}$, and $R^{11}$ are the same or different and are each independently selected from a 5- or 6-membered heterocyclyl group containing 1, 2 or 3 heteroatoms selected from the group consisting of O, N and S, and $Z_2^-$ is a monovalent anion.

10. The process according to claim 1, wherein the phase transfer catalyst is tetrakis(1-piperidyl)phosphonium chloride.

11. The process according to claim 1, wherein X is halogen.

12. The process according to claim 1, wherein the 2-Methylbenzyl compound of the formula (IV) is 2-Methylbenzyl chloride of the formula (IVa)

13. The process according to claim 1, wherein the substantially anhydrous inert organic solvent is selected from aromatic hydrocarbons.

14. The process according to claim 3, wherein the substantially anhydrous inert organic solvent is toluene.

15. The process according to claim 7, wherein the substantially anhydrous inert organic solvent has a water content lower than 0.0001% by weight (based on the total weight of the substantially anhydrous inert organic solvent).

16. The process according to claim 9, wherein the monovalent anion $Z_2^-$ is selected from the group consisting of a halide, hydroxide, hydrogen sulfate, and monomethyl sulfate.

17. The process according to claim 9, wherein the monovalent anion $Z_2^-$ is selected from the group consisting of chloride, bromide, iodide, and hydroxide.

18. The process according to claim 9, wherein the monovalent anion $Z_2^-$ is chloride.

* * * * *